United States Patent [19]

Steinberg et al.

[11] Patent Number: 5,654,996

[45] Date of Patent: Aug. 5, 1997

[54] METHOD AND APPARATUS FOR POSITIONING BLOCKING ELEMENTS IN A COLLIMATOR

[75] Inventors: Todd H. Steinberg, Antioch; Michael John Smidebush, Concord; Robert J. Heck, Pacifica, all of Calif.

[73] Assignee: Siemens Medical Systems, Inc., Iselin, N.J.

[21] Appl. No.: 623,724

[22] Filed: Mar. 29, 1996

[51] Int. Cl.$^6$ ..................................................... A61N 5/10
[52] U.S. Cl. ............................................. 378/65; 378/150
[58] Field of Search ...................... 250/492.3; 378/65, 378/150

[56] References Cited

U.S. PATENT DOCUMENTS 4,794,629  12/1988  Pastyr et al. ............................. 378/65

Primary Examiner—Craig E. Church

Attorney, Agent, or Firm—Heather S. Vance

[57] ABSTRACT

A method and an apparatus for positioning blocking elements (310, 320) in a collimator (4) is provided. The collimator (4) is located in a radiation emitting device (2) delivering a radiation beam (1) to an object (13). The collimator (4) includes a plurality of movable blocking elements (310, 320). The blocking elements (310, 320) are movable for defining an opening (330) for the radiation beam (1). After forming an opening (330) with the blocking elements (310, 320), a calibration tool (400) having a cross bar (410) is inserted in the opening (330) and the cross bar (410) is moved to a defined first position (500) in the opening (408) of the calibration tool. A group of blocking elements is then moved to the cross bar (410). The cross bar (410) is then moved to a defined second position (510) in the opening (408) and the a group of blocking elements is moved to the cross bar (410). The beformentioned steps are repeated until the collimator is calibrated or all the blocking elements (310, 320) are positioned.

23 Claims, 4 Drawing Sheets

5,654,996

METHOD AND APPARATUS FOR POSITIONING BLOCKING ELEMENTS IN A COLLIMATOR

BACKGROUND OF THE INVENTION

1. Technical Field

This invention relates to a method and apparatus for positioning blocking elements in a collimator which is located in a radiation emitting device, and more particularly to a method and an apparatus for positioning blocking elements in a collimator used for radiation treatment.

2. Description of the Related Art

Radiation-emitting devices are generally known and used, for instance, as radiation therapy devices for the treatment of patients. A radiation therapy device generally comprises a gantry which can be swiveled around a horizontal axis of rotation during the course of a therapeutic treatment. A linear accelerator is located in the gantry for generating a high-energy radiation beam (typically, of electrons or photons, that is, X-rays) for therapy. During treatment, this radiation beam is trained on a zone of a patient lying in the isocenter of the gantry rotation.

Contour collimators can be used in radiation therapy. Malignant tissue is destroyed by exposing it to a powerful radiation beam, and at the same time, it is important that healthy tissue not be damaged. For this purpose, in radiation therapy equipment, a contour collimator is placed between the source of radiation and the irradiated area. This limits the radiation exposure to essentially the malignant tissue.

Usually, contour collimators comprise movable aperture plates which are driven by electric motors. In recent years, multileaf collimators have contained two stacks of aperture plates. Each aperture plate is driven by a separate electrical motor such that apertures of various shapes are created between the opposing aperture plates. Such a multileaf contour collimator has been described in U.S. Pat. No. 5,165,106. This contour collimator has rotatably mounted aperture plates and the plates of each stack can be rotated around one axis to define an opening. Similarly, linear contour collimators can comprise two stacks of aperture plates which are linearly movable against each other in the same plane. These plates are also driven by electric motors.

Before treatment, an object (e.g., a patient) may be scanned with a computer tomograph (CT) and/or treatment may be simulated with a diagnostic X-ray unit. These devices localize the spot in the body to be irradiated and identify surrounding critical organs. The physician determines a method of treatment based on patient weight, patient age, and type and size of the diseased area. Data from the CT and the simulator along with the machine type are used in the treatment planning process to calculate dose levels to the treatment site and radiation exposure to surrounding tissue. When the physician approves a plan, it is transferred to a verify-and-record system. The contour collimator is then adjusted according to the treatment plan. Correct calibration of the contour collimator is critical.

Calibration of the contour collimator can be done by moving the aperture plates to defined positions and then setting a controller to values corresponding to these defined positions. This is done, for instance, by temporarily replacing the radiation beam by a light beam, so that a projection of the opening can be seen on graph paper in the plane of the object. Values read from the graph paper are then input in the controller as reference points. This method, while providing adequate calibration, is very time consuming. In light of this, there is a need for a simple and easy way to calibrate a collimator and more particularly to calibrate the positions of the plurality of aperture plates in a multileaf contour collimator.

SUMMARY OF THE INVENTION

According to the invention, a plurality of movable blocking elements located in a collimator are positioned. The collimator is in a radiation emitting device which delivers a radiation beam to an object. In the preferred embodiment of the invention, the blocking elements are moved to form an opening for the radiation beam. A calibration tool is then inserted over the opening. This calibration tool includes a cross bar which is moved to a defined position in the opening. One or more of the blocking elements is then moved until the blocking element(s) stops against the cross bar. A position indicator can be used to measure the position of the stopped blocking element(s). In one embodiment of the present invention, the position of the stopped blocking element(s) is then scanned and stored. The stored position of the stopped blocking element(s) is used to calibrate the collimator. In another embodiment of the invention, the measured position of the stopped blocking element(s) is used to check the quality of the collimator. In yet another embodiment of the invention, the cross bar is continually repositioned and each of the blocking elements positioned until all the blocking elements are placed within a desired pattern.

DETAILED DESCRIPTION

In the preferred embodiment, the present invention is used with a system for delivering X-ray radiation to a patient. The invention limits the amount of radiation needed by using a multileaf collimator located in the beam path from the radiation source. The invention may also be used to calibrate a collimator for any type of energy, for example, electrons (instead of X-rays), to any type of object (not just a human patient).

Figure 1:
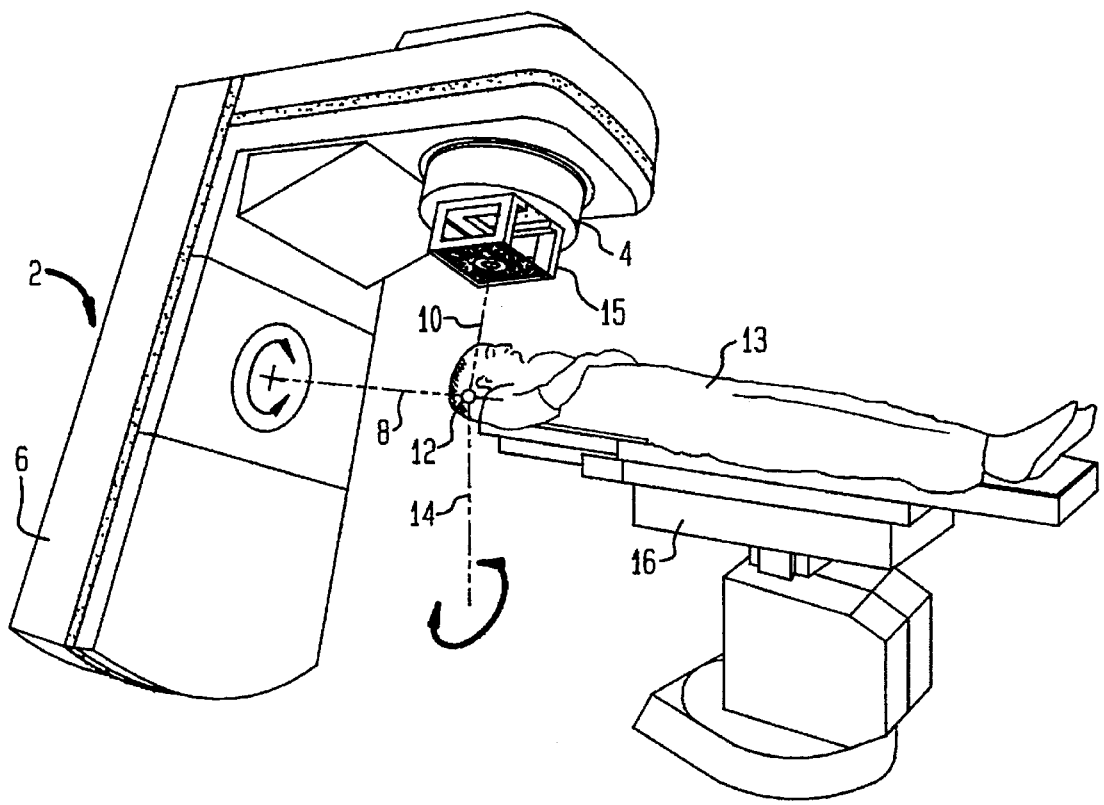
FIG. 1 shows a diagram of a radiation therapy device.

FIG. 1 shows a portion of a radiation treatment device 2 of common design. The radiation treatment device comprises a gantry 6 which can be swiveled around a horizontal axis of rotation 8 in the course of a therapeutic treatment. A collimator 4 and an equipment holder 15 are fastened to a projection of gantry 6. To generate the high-powered radiation required for the therapy, a linear accelerator is located within gantry 6. The axis of the radiation bundle emitted from the linear accelerator and gantry 6 is designated by 10.

As stated above, electron, photon, or any other detectable radiation can be used for therapy.

During treatment the radiation beam is trained on a zone 12 of an object 13 (e.g., a patient who is to be treated and who lies at the isocenter of the gantry rotation). The rotational axis 8 of gantry 6, the rotational axis 14 of the area to be treated, and the beam axis 10 all preferably intersect in the isocenter. The construction of such a radiation treatment device is described in general in a brochure "Digital Systems for Radiation Oncology", Siemens Medical Laboratories, Inc. A91004-M2630-B358-01-4A00, September 1991.

The area of a patient that is irradiated is known as the "field" which is defined by collimator 4. Collimator 4 comprises plates or jaws that are substantially impervious to the emitted radiation. Thus, collimator 4 is mounted between the radiation source and the patient to limit the field of radiation. Areas of the body (e.g., healthy tissue not to be treated) are therefore subjected to as little radiation as possible.

In the preferred embodiment of the invention, at least one of the plates is movable, so that the distribution of radiation over the field need not be uniform (i.e., one region can be given a higher dose than another). Furthermore, the gantry can preferably be rotated so as to allow different beam angles and radiation distributions without having to move the patient. Moreover, plates are not the only type of beam-shielding devices that may be used. For example, some other form of beam collimator, jaw, wedge compensator or other aperture device may be used to limit radiation distributions. All of these plates, leaves, jaws, wedge compensators and the like are referred to as blocking elements. Thus, the aperture device itself may act as the beam-shielding device, or the various beam-shielding devices can be combined to limit the field.

Radiation treatment device 2 also includes a conventional treatment unit (not shown) which is usually located apart from gantry 6 and treatment table 16. The treatment unit is utilized by a therapist. Preferably, the radiation treatment device 2 is located in a separate room to protect the therapist from radiation. The treatment unit includes an output device, such as a visual display unit or monitor, and a keyboard. The treatment unit is routinely operated by the therapist who administers delivery of radiation treatment as prescribed by an oncologist. By using the keyboard, the therapist can program the treatment unit so that the prescribed radiation is delivered to the patient. A program for the treatment unit can also be input via another input device such as a data storage device or through data transmission.

Figure 2:
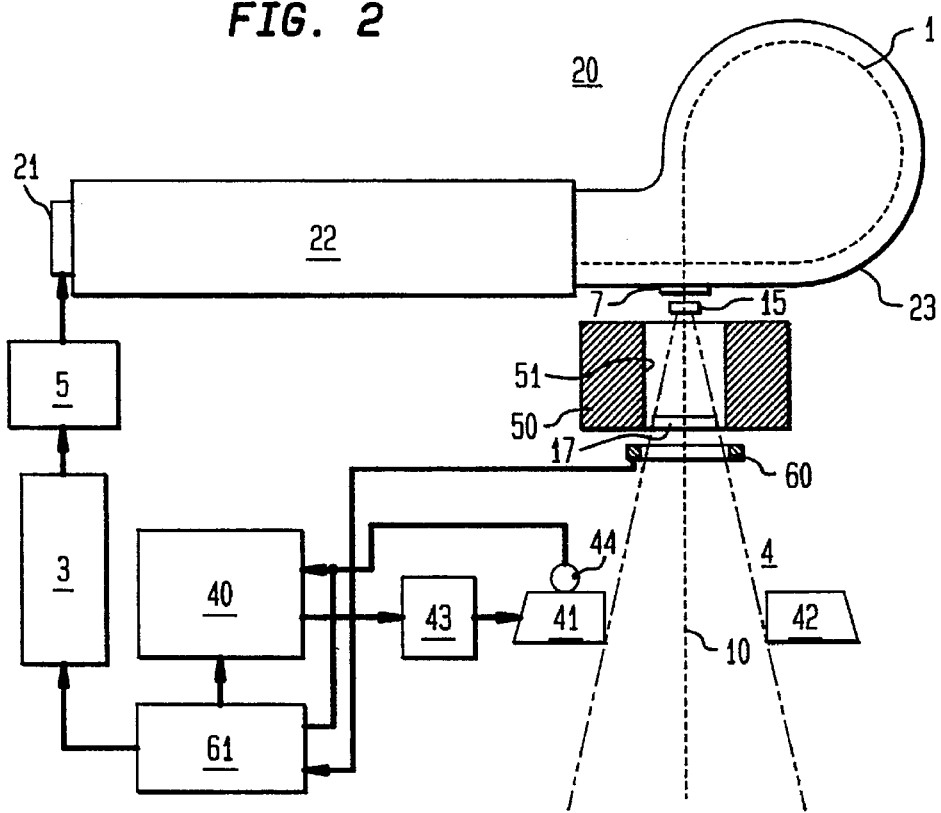
FIG. 2 is a block diagram illustrating portions of a control unit and a beam generation system in the radiation therapy device of FIG. 1.

FIG. 2 shows portions of a control unit and a beam generation system in the radiation therapy device of FIG. 1. An electron beam 1 is generated in an electron accelerator 20. Accelerator 20 comprises an electron gun 21, a wave guide 22 and an evacuated envelope or guide magnet 23. A trigger system 3 generates injector trigger signals and supplies them to injector 5. Based on these injector trigger signals, injector 5 generates injector pulses. These injector pulses are fed to electron gun 21 in accelerator 20 for generating electron beam 1. Electron beam 1 is accelerated and guided by wave guide 22. For this purpose, a high frequency (HF) source is provided. This HF source supplies radio frequency (RF) signals for the generation of an electromagnetic field which is then supplied to wave guide 22. The electrons injected by injector 5 and emitted by electron gun 21 are accelerated by this magnetic field in wave guide 22, and they exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, the beam is sent through a measuring chamber 60, which ascertains the distribution dose. If the radiation beam is an x-ray beam, the scattering foils are usually replaced by a target.

As stated above, collimator 4 is located in the path of radiation beam 1. Collimator 4 is, for example, a multileaf contour collimator. Collimator 4 includes plates or jaws 41, 42 which are moveable in a direction substantially perpendicular to axis 10 of radiation beam 1. Additional plates can be provided in a similar manner. Plates 41, 42 are moved by a drive unit 43. Drive unit 43 includes an electric motor which is coupled to plate 41 and which is controlled by a motor controller 40. Motor controller 40 is coupled to a dose control unit which includes a dosimetry controller 61 for providing set values for the radiation beam dose rate in correlation with the position of plate 41. The dose rate of the radiation beam is measured by measuring chamber 60. Control unit 40 receives its position information from gantry 6 and information about the radiation emitted from the radiation source 15 from measuring chamber 60.

Figure 3:
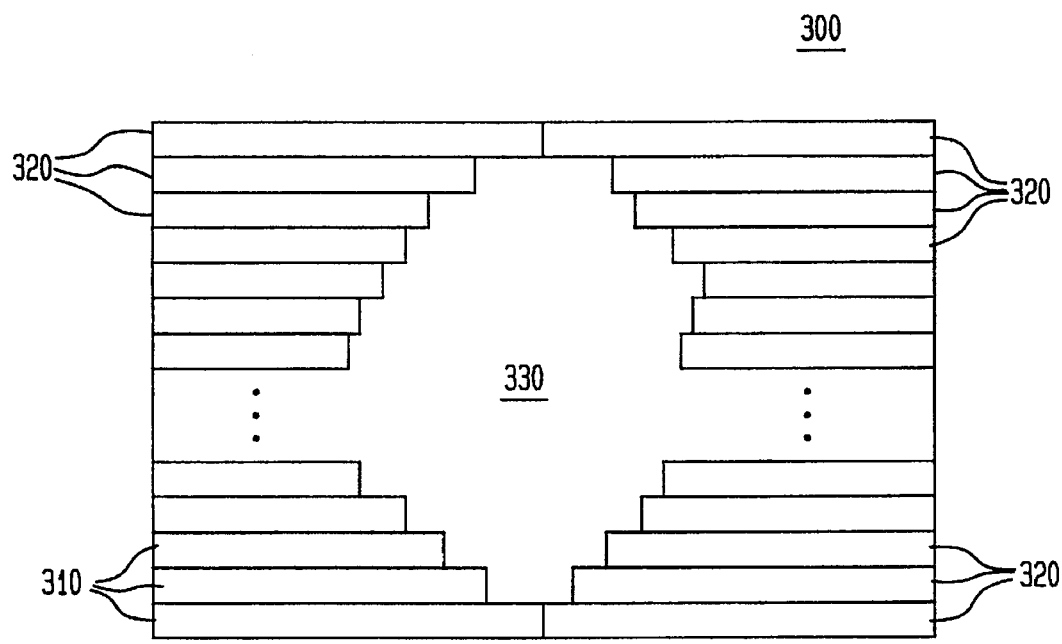
FIG. 3 shows a diagram of a multileaf contour collimator.

FIG. 3 shows a contour collimator 300 comprising two stacks of plates/leaves 310 and 320 which are movable against each other. Leaves 310, 320 can be straight rectangulars as shown in FIG. 3, or they can be curved or rounded rectangular like elements. Each stack of leaves 310, 320 is usually driven by motors (e.g., electrical stepper motors), one motor for each leaf. Any other type of driving means can also be used to move leaves 310, 320. Leaves 310, 320 form an opening 330 which corresponds to an area to be irradiated in the body of a patient, whereby leaves 310, 320 protect healthy tissue from damage caused by radiation beam 1. To define opening 330 in the correct size and shape, leaves 310, 320 have to be carefully positioned. For this purpose, calibration of each of the leaves' positions with respect to reference positions is performed before the radiation is delivered. Preferably, this calibration is also performed later on, multiple times during the treatment.

Figure 4:
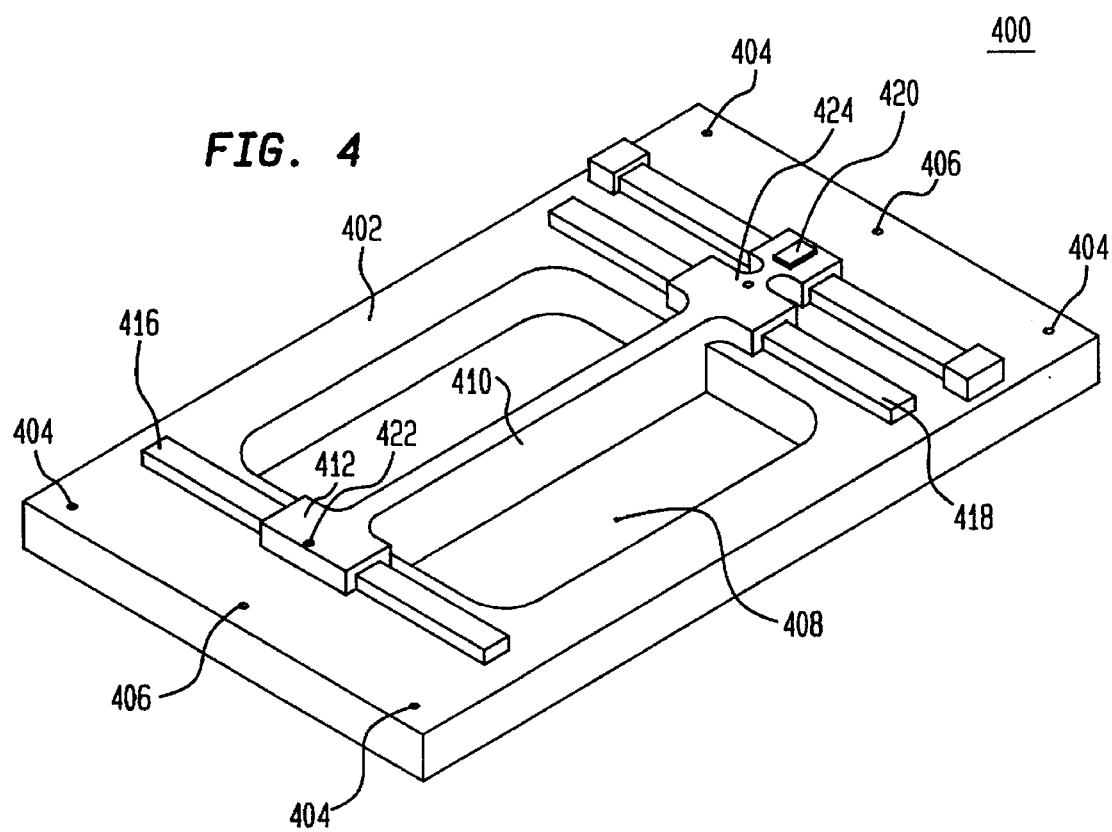
FIG. 4 shows a perspective view of a calibration tool with a cross bar.

FIG. 4 shows a perspective view of a calibration tool 400 for calibrating each of the leaves' positions. Tool 400 includes a base frame 402 provided with screw holes 404 and holes 406 for alignment or adjustment pins. One advantage of a hole/pin arrangement is that a user can quickly modify the existing calibrator. Pegs can be used instead of pins, and the pins/pegs can be located on base frame 402 while the holes are located on collimator 4. In another embodiment of the present invention, base frame 402 can have long narrow protrusions which slide into long narrow slot located on the bottom of collimator 4. Thus, any conventional mounting technique can be used to mount tool 400 on collimator 4.

Base frame 402 also has an opening 408. In this opening 408, a cross arm 410 is movable in the direction of the y-axis as indicated by arrows 411. Cross arm 410 can be a one part piece or can be composed of multiple parts, and it is slidably mounted with slides 412 and 414 on rails or bars 416 and 418, respectively, on either side. Thus, cross arm 410 extends in the direction of the x-axis and drops down through opening 408 in the direction of the z-axis, and bars 416 and 418 extend in the direction of the y-axis. Base frame 402, cross bar 410 and rails/bars 416, 418 are all preferably made of a metal, such as stainless other type of steel, which is easy to machine precisely. In the preferred embodiment, slides 412, 414 are preloaded to eliminate any gap between slides 412, 414 and rails 416, 418. Slides 412, 414 can also include precision bearings (e.g., needle or ball bearings) or any bearing that provides for smooth gliding along rails 416, 418. Additionally, a position indicator 420 is provided which indicates the exact position of cross arm 410 over opening 408. Position indicator 420 can be part number 572-211-10 which is commercially available from Mitutoyo, or a commercially available vernier. The Mitutoyo position indicator is a non-contact sensing device. Position indicator 420 can also utilize optical position encoding as opposed to friction or gears for position sensing. The position indicator can be used to provide an electronic display (e.g., LCD or LED display) for displaying the measured position. While the electronic display makes the device user friendly, the readout of the position indicator does not have to be electronic; any conventional display means can be utilized. The contents of this electronic display can be operator programmable.

Position indicator 420 is slidably attached to position bar 421. To place cross arm 410 in a defined location, clamps 422 and 424 can be arranged on rails 416, 418. Clamps 422 and 424 can be replaced by a single clamp or by one or more adjustment pins. Furthermore, clamps 422 and 424 can be arranged in any position which holds the cross bar in position. Index mechanism 430 is an optional device used for maintaining a consistent zero position on the measuring scale. When index mechanism 430 is used, an index pin 432 is inserted through index mechanism 430 and into base frame 402. The position of cross bar 410 is then read by position indicator 420. If the read position is not zero, position indicator 420 is recalibrated to read zero. After the absolute position is determined, index pin 432 is removed.

Figure 5:
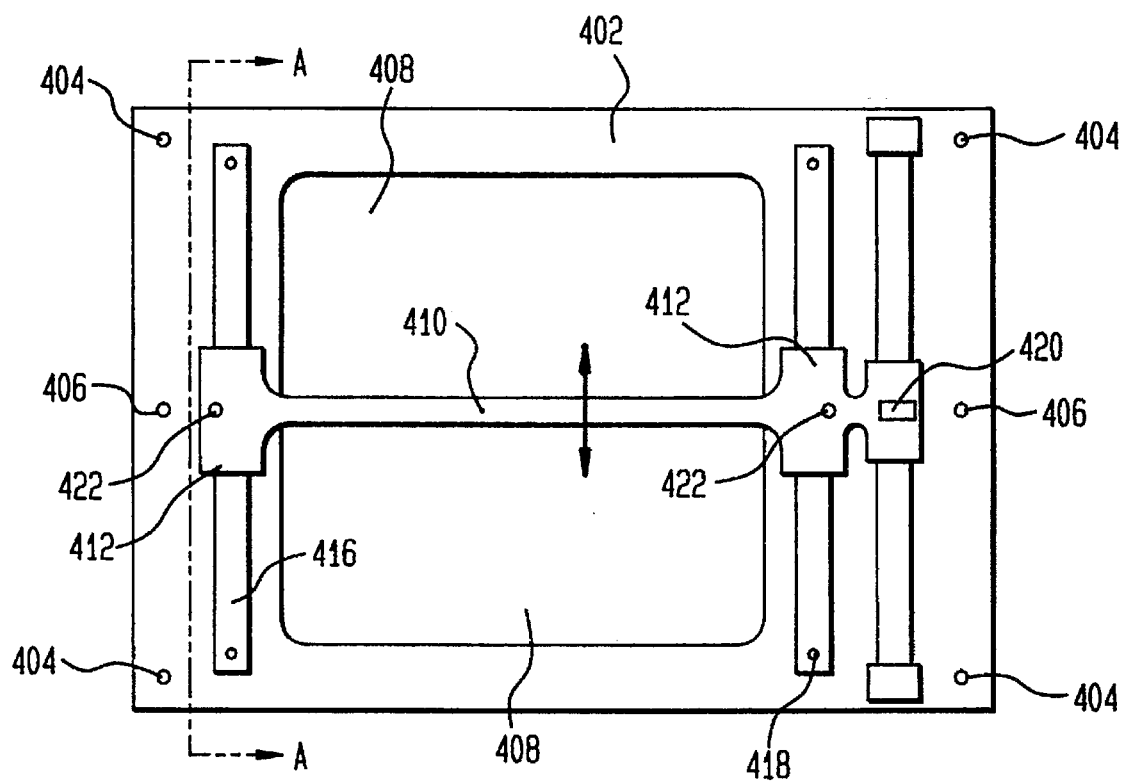
FIG. 5 shows a top view of a calibration tool with a cross bar.
Figure 6:
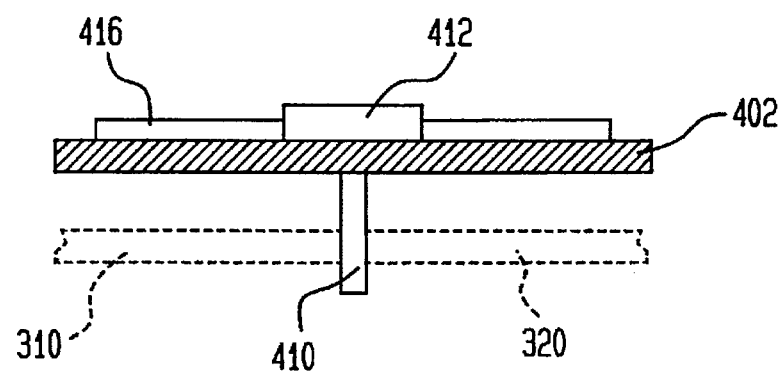
FIG. 6 shows a side view of a calibration tool with a cross bar.

FIG. 5 shows a top view of tool 400. Tool 400 includes base frame 402 which contains opening 408 and screw holes 404 and holes 406 for adjustment pins. Cross arm 410 is arranged on bars 416 and 418, and position indicator 420 shows the exact position of cross arm 410 in the direction of the y-axis. FIG. 6 shows a side view of tool 400 which is a section along arrow A—A in FIG. 5. This view of tool 400 shows how cross arm 410 drops down through the opening in base frame 402 in the direction of the z-axis. Leaves 310, 320 of the multileaf collimator (see FIG. 3) are indicated with dashed lines.

The present invention can be used for three different modes of operation. In the first mode of operation, the collimator is calibrated. In the second mode of operation, the invention is used for quality assurance. In the third mode of operation, leaves 310 and 320 are all positioned by tool 400. During the calibration of multileaf collimator 300 (in the first mode of operation), leaves 310 and/or 320 can be moved by electric motors against cross bar 410. After this occurs, the positions of the leaves are stored together with the position of cross bar 410. The positions of the leaves can be measured by a code wheel which is connected to the motors. Then, cross bar 410 can be moved to a different known position, and again leaves 310, 320 are moved against cross bar 410 and their sensed positions stored. After these sensed positions are stored in a memory unit, they can be compared with the inputted pattern desired for radiation treatment. A calibration table can then be created to show how the sensed positions compare to the inputted/pre-stored pattern. The sensed positions are used as calibration points when leaves 310 and 320 are later positioned to reflect the inputted pattern.

To begin the calibration process in the first mode of operation, gantry 6 (see FIG. 1) is rotated to a position which makes it accessible to a user. Accessory holder 15 is then removed, and leaves 310, 320 are moved outwardly to positions in which opening 330 (see FIG. 3) has a size of, for example, 40×40 cm. Accessory holder 15 is then replaced by tool 400. For this purpose, base frame 402 of tool 400 is attached to the collimator with, for example, screws through screw holes 404 and indexed with taper pins through holes 406 (see FIG. 5).

Figure 7:
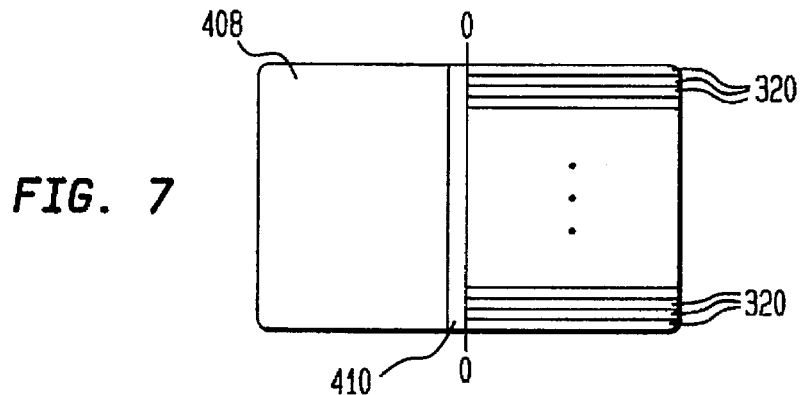
FIG. 7 shows a cross bar at a position "right side zero"
Figure 8:
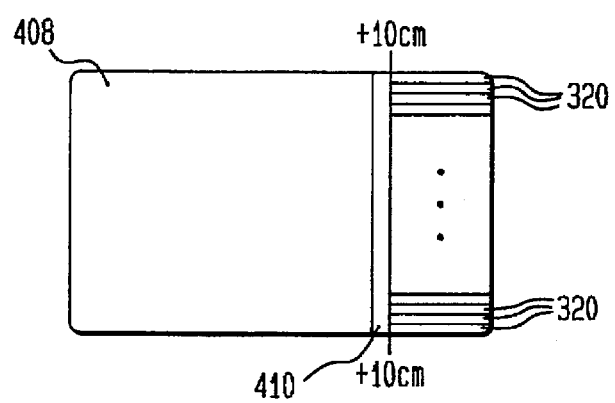
FIG. 8 shows a cross bar at a position "right side 10 cm"

To carry out the calibration process, cross arm 410 is positioned in a defined location (e.g., the center position) and then pinned in that position. As stated above, indexing mechanism 430 and index pin 432 can be used to pin cross arc 410 in the defined location. Position indicator 420 is then reset to position "0". Since cross arm 410 has a given thickness, leaves 310, 320 are not in the true zero position. Therefore, cross arm 410 is unclamped and moved to a position "right side zero" 500, as shown in FIG. 7. Leaves 320 can be moved by the electric motors to cross arm 410. In the preferred embodiment, when leaves 320 touch cross bar 410 they stop. For example, when the motors (or other driving means) moving leaves 320 sense the resistance or current increase caused by contacting cross bar 410, they can be programmed to automatically stop/shut off. When leaves touch cross bar 410 they are in the zero position. This zero position is regarded as a reference position for leaves 320 on position indicator 420. After this reference position is determined, leaves 320 are moved to their open positions. Cross bar 410 is then unclamped and moved to a defined right side position (e.g., "right side 10 cm" 510) as shown in FIG. 8. In this position, cross bar 410 is clamped and leaves 320 are moved toward cross bar 410 until they touch the cross bar and stop. Their positions are then stored as right side 10 cm reference positions.

Figure 9:
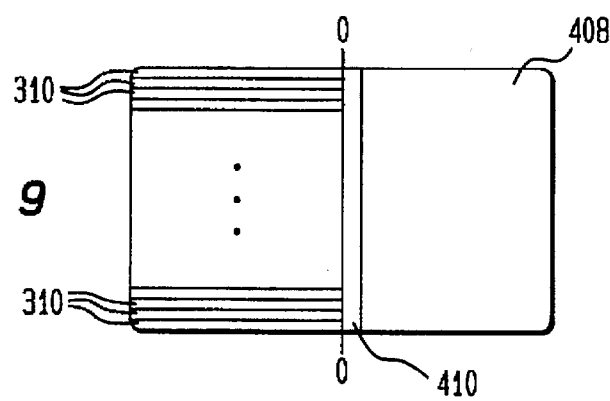
FIG. 9 shows a cross bar at a position "left side zero"
Figure 10:
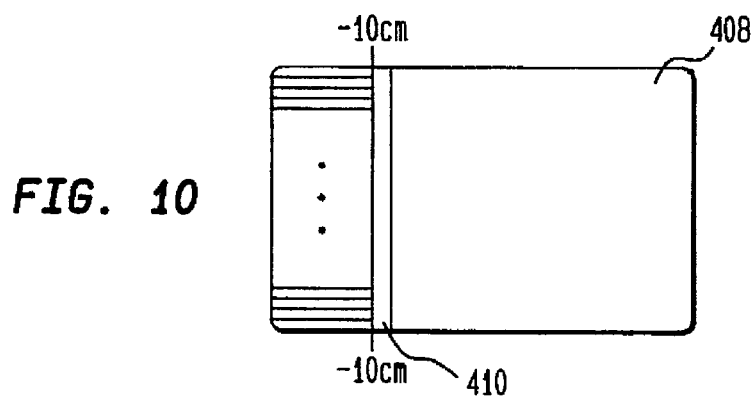
FIG. 10 shows a cross bar at a position "left side 10 cm".

After the positions of leaves 320 are scanned and stored, the same steps are repeated for the left side zero 520 and the left side 10 cm 530 positions as indicated in FIGS. 9 and 10. Also, position indicator 420 can be connected to controller 40 during the calibration process. Thus, controller 40 can assist in the calibration of the positions of leaves 310, 320. Furthermore, an electric motor can be provided on tool 400 to move cross bar 410 to the defined positions. Any other form of driving device can also be used to move cross bar 410. In this arrangement, the various positions of cross bar 410 are measured by position indicator 420 and transmitted to controller 40 such that the leaves' positions correspond to the information from position indicator 420.

In another embodiment of the invention, a four-point calibration can be used for each of leaves 310, 320. For example, leaves 310 can be calibrated at the 20 cm, 10 cm, 0 and −10 cm left side positions, and leaves 320 can be calibrated at the 20 cm, 10 cm, 0 and −10 cm right side positions. Thus, any combination of points (e.g., 20 cm, 10 cm and 5 cm; 1 cm, 2 cm, 3 cm and 12 cm; etc.) can be used for calibration. In yet another embodiment of the invention, a software program can be used to randomly select calibration points. This software program can also be used to automatically perform the calibration. Cross bar 410 is then moved to the first selected point, and position indicator 420 provides the corresponding measured position. The measured position is provided to the software which then compares the measured position with the selected point. If the two positions do not match, the software can send a signal which recalibrates position indicator 420. This is repeated for each of the randomly selected points. This software can also be used with predetermined points. Again, cross bar 410 is moved to the first of the predetermined points, and position indicator 420 provides the corresponding measured position. If the positions do not match, the software recalibrates position indicator 420. This is again repeated for each of the predetermined points.

In the second mode of operation, the present invention is used for automatic quality control which can take place without calibration or after calibration. For this automatic quality control, cross bar 410 is moved on a random basis to various positions within opening 408. These positions are then measured by position indicator 420, and leaves 310, 320 are moved to cross bar 410. The position values are then compared with the expected position values. Quality assurance can also be carried out by driving leaves 310, 320 to defined positions, moving cross bar 410 to leaves 310, 320 and then checking whether cross bar 410 is in the expected position.

In the third mode of operation, leaves 310 and 320 are all positioned by tool 400. In this embodiment, cross bar 410 is used to set leaves 310 and 320 in the pre-stored pattern used for radiation treatment. Thus, tool 400 is not used for calibration in this embodiment. Again, accessory holder 15 is replaced by tool 400 in this third mode of operation. Instead of placing cross bar 410 in the specific positions indicated above, cross bar 410 can be placed in any positions within opening 408 as long as these positions are input to controller 40 as positions within the pre-stored pattern. Cross bar 410 is used to set each one of leaves 310 and 320 in their desired positions. When this occurs, cross bar 410 is continually repositioned until each of leaves 310 and 320 are positioned. For example, a first group of leaves (e.g., the 3 most center leaves within set of leaves 320, see FIG. 3) might be positioned by cross bar 410 at the right side 10 cm (as shown in FIG. 8), the second group of leaves at the right side 9 cm, the third group of leaves at the right side 8 cm, and so on until the last group of leaves within set of leaves 320 (e.g., the 2 most outer leaves) are positioned at the right side of zero (as shown in FIG. 7). This sequence of repositioning cross bar 410 and positioning each leaf is then done for the set of leaves 310 on the left side of opening 408 (see FIGS. 9 and 10). FIG. 3 provides an example of how leaves can be positioned by tool 400 in a desired/pre-stored pattern. As stated above, the positioned leaves 310, 320 form opening 330 which corresponds to the area to be irradiated in the object. Thus, by accurately positioning leaves 310, 320, healthy tissue is protected from damage cased by the radiation beam.

Furthermore, for quality assurance purposes, the calibration of the collimator and/or the position of the leaves within the collimator can be checked by examining the resulting radiation beam pattern. This is done by removing the object and exposing a special film to the beam pattern. The beam pattern is then captured on the film such that the radiation exposure can be monitored. As an alternative, an electronic scanning device can be used instead of the film to capture the beam pattern. All of the leaves' positions can be checked in this manner.

What is claimed is:

1. A method for positioning a plurality of movable blocking elements in a collimator, wherein the collimator is in a radiation emitting device delivering a radiation beam to an object, the method comprising the steps of:
   a) moving the blocking elements to form an opening for the radiation beam;
   b) inserting a calibration tool over the opening, the calibration tool having a cross bar;
   c) moving the cross bar to a defined position in the opening; and
   d) moving at least one of the blocking elements until the blocking element stops against the cross bar.

2. A method as defined in claim 1, further comprising the step of scanning and storing the position of the stopped blocking element.

3. A method as defined in claim 2, further comprising the step of calibrating the collimator by using the stored position of the stopped blocking element.

4. A method as defined in claim 2, further comprising the step of checking quality of the collimator calibration by using the stored position of the stopped blocking element.

5. A method as defined in claim 1, further comprising the step of repeating steps c) and d) until the blocking elements form a desired pattern.

6. A method as defined in claim 1, wherein the blocking elements are at least one of leaves, plates, jaws and wedge compensators.

7. A method as defined in claim 1, wherein the cross bar is clamped in the defined position.

8. A method as defined in claim 1, wherein the cross bar is moved into the defined position by an electric motor.

9. A method as defined in claim 1, wherein the defined position of the cross bar are measured by a position indicator.

10. A method as defined in claim 1, wherein values corresponding to the defined position of the cross bar are transferred to a control unit.

11. A method for calibrating a collimator in a radiation emitting device delivering a radiation beam to an object, wherein the collimator includes at least one pair of movable blocking elements for defining an opening for the radiation beam, the method comprising the steps of:
   a) moving the blocking elements to form the opening;
   b) inserting a calibration tool having a cross bar in the opening;
   c) moving the cross bar to a defined first position in the opening;
   d) moving a first of the pair of blocking elements to the cross bar;
   e) scanning and storing the position of the first of the pair of blocking elements;
   f) moving the cross bar to a defined second position in the opening;
   g) moving the first of the pair of blocking elements to the cross bar;
   h) scanning and storing the new position of the first of the pair of blocking elements;
   i) repeating steps c) through h) for the other pair of blocking elements; and
   j) calibrating the collimator by using the stored positions of the pair of blocking elements.

12. A method as defined in claim 11, wherein each of the positions of the cross bar are measured by a position indicator.

13. A method as defined in claim 11, wherein values corresponding to each of the positions of the cross bar are transferred to a control unit.

14. An apparatus for position a plurality of blocking elements in a collimator, wherein the collimator is in a radiation emitting device delivering a radiation beam to an object, and wherein the blocking elements are movable for defining an opening for the radiation beam, the apparatus comprising:

a base frame having an opening, the base frame being mountable on the collimator;

a cross bar movably attached to the base frame and extending through the opening; and positioning means for moving the blocking elements against the cross bar.

15. An apparatus as defined in claim 14, further comprising a position indicator for measuring a position of the cross bar.

16. An apparatus as defined in claim 14, further comprising memory means for storing the measured position of the movable blocking elements, whereby the collimator is calibrated with the stored measured position of the movable blocking element.

17. An apparatus as defined in claim 14, wherein the cross bar is slidably attached to the base frame.

18. An apparatus as defined in claim 17, wherein the cross bar includes slides capable of sliding on bars coupled to the base frame.

19. An apparatus as defined in claim 14, wherein the cross bar includes clamp means for clamping it in multiple positions.

20. An apparatus as defined in claim 14, wherein the blocking elements are at least one of leaves, plates, jaws and wedge compensators.

21. A system for position a plurality of blocking elements, comprising:

a radiation emitting device delivering a radiation beam to an object, the blocking elements being movable for defining an opening for the radiation beam;

a collimator located in the radiation emitting device, the blocking elements being inside the collimator; and a tool coupled to the collimator, the tool comprising:

a base frame having an opening, the base frame being mountable on the collimator;

a cross bar movably attached to the base frame and extending through the opening; and positioning means for moving the blocking elements against the cross bar.

22. A system as defined in claim 21, further comprising a position indicator for measuring a position of the cross bar.

23. A system as defined in claim 21, further comprising memory means for storing the measured position of the movable blocking elements, whereby the collimator is calibrated with the stored measured position of the movable blocking element.

* * * * *